(12) United States Patent
Creston et al.

(10) Patent No.: US 11,529,191 B2
(45) Date of Patent: Dec. 20, 2022

(54) AUXILIARY ELECTROSURGICAL RETURN VIA CUTTING GUARD

(71) Applicant: Covidien LP, Mansfield, MA (US)

(72) Inventors: Brian J. Creston, Madison, CT (US); Jacob C. Baril, Norwalk, CT (US); Scott J. Prior, Shelton, CT (US); Saumya Banerjee, Hamden, CT (US); Ernest A. Addi, Middletown, CT (US); Amy L. Kung, Hamden, CT (US); Christopher M. Meehan, New Haven, CT (US); Thomas A. Zammataro, North Haven, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 281 days.

(21) Appl. No.: 16/883,477

(22) Filed: May 26, 2020

(65) Prior Publication Data

US 2021/0369345 A1 Dec. 2, 2021

(51) Int. Cl.
*A61B 18/16* (2006.01)
*A61B 18/12* (2006.01)

(52) U.S. Cl.
CPC .......... *A61B 18/16* (2013.01); *A61B 18/1206* (2013.01); *A61B 2018/126* (2013.01)

(58) Field of Classification Search
CPC . A61B 17/3423; A61B 18/00; A61B 18/1206; A61B 18/1402; A61B 18/16; A61B 2017/00951; A61B 2017/345; A61B 2018/00178; A61B 2018/126; A61B 2018/1412; A61B 2090/08021
See application file for complete search history.

(56) References Cited

U.S. PATENT DOCUMENTS

| | | | | |
|---|---|---|---|---|
| 4,226,247 | A | * | 10/1980 | Hauser ................. A61B 5/259 607/152 |
| 4,237,886 | A | * | 12/1980 | Sakurada ............... A61N 1/04 252/511 |
| 5,578,000 | A | | 11/1996 | Greff et al. |
| 5,941,873 | A | | 8/1999 | Korenfeld |
| 6,033,362 | A | | 3/2000 | Cohn |
| 6,544,210 | B1 | | 4/2003 | Trudel et al. |
| 7,789,946 | B2 | | 9/2010 | Schultz et al. |

(Continued)

*Primary Examiner* — Khadijeh A Vahdat
(74) *Attorney, Agent, or Firm* — Carter, DeLuca & Farrell LLP

(57) ABSTRACT

An auxiliary return system for use with a bipolar electrosurgical device includes a tissue guard defining an open proximal end, an open distal end, and a lumen extending therethrough between the open proximal end and the open distal end. A ground plate is disposed along an inner peripheral surface of the lumen and is operably coupled to a first end of a ground wire extending from the tissue guard. A coupling is included having a bore defined therein for receiving a cable from an electrosurgical device therethrough, the cable including active and ground leads. The coupling has a flange extending therefrom defining a receptacle therein configured to operably receive a plug connected to a second end of the ground wire. The receptacle is configured to provide electrical continuity between the ground lead disposed within the cable and the plug coupled to the ground wire which, in turn, provides electrical continuity to the ground plate.

3 Claims, 3 Drawing Sheets

(56) References Cited

U.S. PATENT DOCUMENTS

| | | |
|---|---|---|
| 7,901,353 B2 | 3/2011 | Vayser et al. |
| 9,427,288 B1 | 8/2016 | Chenger et al. |
| 10,076,358 B2 | 9/2018 | Zergiebel et al. |
| 2005/0054993 A1 | 3/2005 | Falahee |
| 2006/0247673 A1 | 11/2006 | Voegele et al. |
| 2012/0089093 A1 | 4/2012 | Trusty |
| 2013/0184536 A1 | 7/2013 | Shibley et al. |
| 2014/0330285 A1 | 11/2014 | Rosenblatt et al. |
| 2016/0158468 A1 | 6/2016 | Tang et al. |
| 2017/0049427 A1 | 2/2017 | Do et al. |
| 2017/0325657 A1 | 11/2017 | Prior |
| 2018/0008250 A1 | 1/2018 | Joseph |
| 2018/0049771 A1 | 2/2018 | Rhemrev-Pieters |

\* cited by examiner

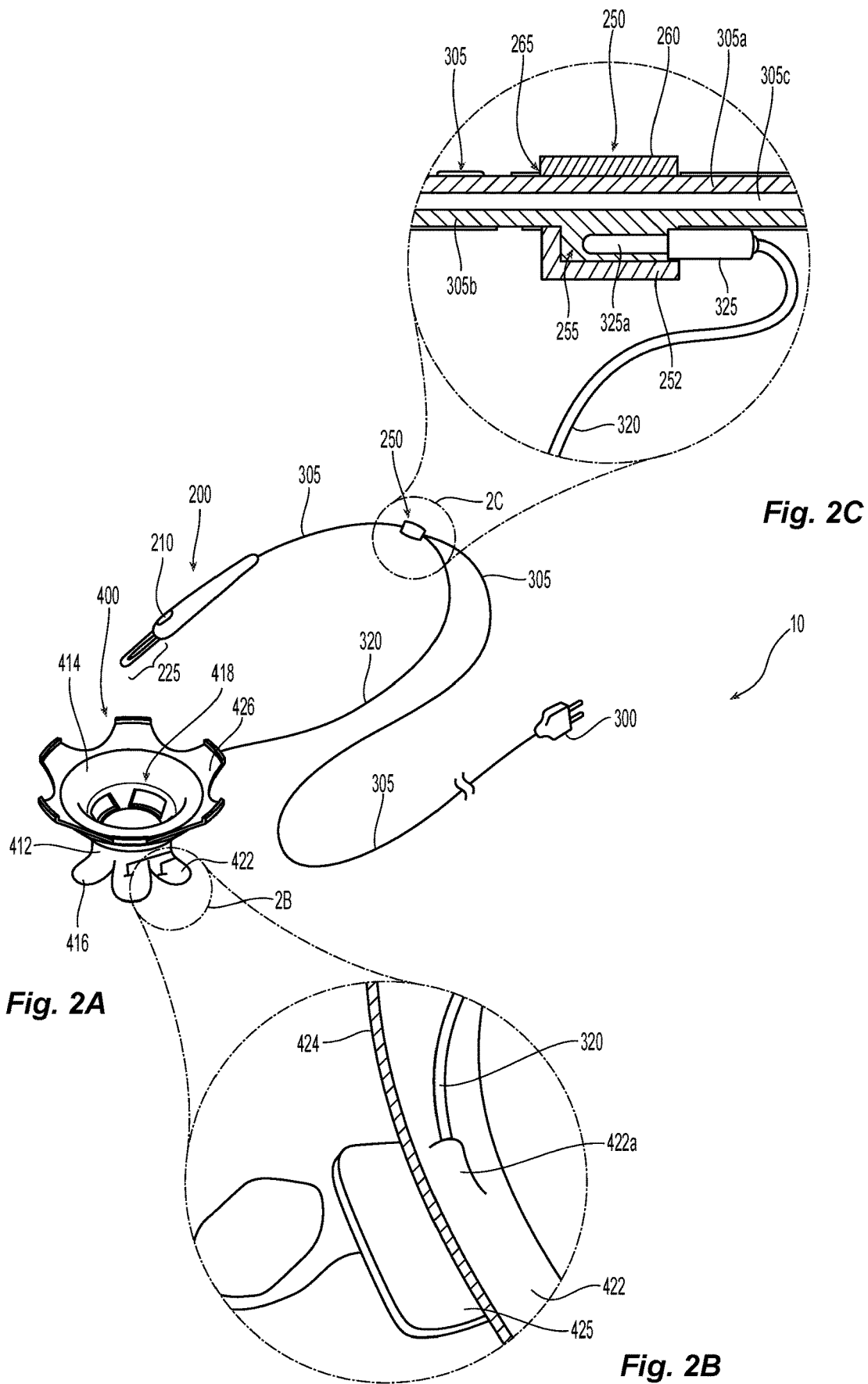

AUXILIARY ELECTROSURGICAL RETURN VIA CUTTING GUARD

FIELD

The present disclosure relates to tissue specimen removal and, more particularly, to tissue guards and systems incorporating the same for use in tissue specimen removal procedures and other electrosurgical surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically electrosurgical instruments such as bipolar electrosurgical pencils may be utilized for this purpose.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an auxiliary return system for use with a bipolar electrosurgical device that includes a tissue guard defining an open proximal end, an open distal end, and a lumen extending therethrough between the open proximal end and the open distal end. A ground plate is disposed along an inner peripheral surface of the lumen and is operably coupled to a first end of a ground wire extending from the tissue guard. A coupling is included having a bore defined therein for receiving a cable from an electrosurgical device therethrough, the cable including active and ground leads. The coupling has a flange extending therefrom defining a receptacle therein configured to operably receive a plug connected to a second end of the ground wire. The receptacle is configured to provide electrical continuity between the ground lead disposed within the cable and the plug coupled to the ground wire which, in turn, provides electrical continuity to the ground plate.

In aspects according to the present disclosure, the receptacle of the coupling is configured to operably receive a banana plug. In other aspects according to the present disclosure, the receptacle of the coupling is configured to operably connect to the cable of the electrosurgical device.

In aspects according to the present disclosure, the electrosurgical device is an electrosurgical pencil. In other aspects according to the present disclosure, the ground wire operably couples to the ground plate through a pocket defined in an outer peripheral surface of the tissue guard.

Provided in accordance with other aspects of the present disclosure is a tissue guard for use with a bipolar electrosurgical device that includes a body defining an open proximal end, an open distal end, and a lumen extending therethrough between the open proximal end and the open distal end. A ground plate is disposed along an inner peripheral surface of the lumen. A ground wire electrically couples at a first end to the ground plate and extends through the body of the tissue guard, a second end of the ground wire is adapted to electrically engage a coupling attached to a return from an electrosurgical device thereby providing electrical continuity between the ground plate and the return.

In aspects according to the present disclosure, the electrosurgical device is an electrosurgical pencil. In other aspects according to the present disclosure, the ground wire operably couples to the ground plate through a pocket defined in an outer peripheral surface of the tissue guard.

Provided in accordance with other aspects of the present disclosure is a tissue guard for use with a bipolar electrosurgical device that includes a body defining an open proximal end, an open distal end, and a lumen extending therethrough between the open proximal end and the open distal end. The body includes an elongated channel defined therealong terminating in a pocket defined through an outer peripheral surface thereof. The pocket housing a wire connector therein. A ground tab is disposed along an inner peripheral surface of the lumen in concentric registration with the pocket and in electrical communication with the connector. An electrically conductive layer is disposed along an inner peripheral surface of the lumen of the body, the electrically conductive layer is disposed in electrical communication with the ground tab. A ground wire is electrically coupled at a first end to the wire connector and extends through the elongated channel to a second end adapted to electrically engage a coupling attached to a return from an electrosurgical device thereby providing electrical continuity between the electrically conductive layer and the return.

In aspects according to the present disclosure, the electrosurgical device is an electrosurgical pencil. In other aspects according to the present disclosure, the distal end of the body is oblong and includes a long petal and a short petal.

In aspects according to the present disclosure, the elongated channel defined in the body provides rigidity to the longer petal of the body of the tissue guard. In other aspects according to the present disclosure, the elongated channel defined in the body is formed by adding a material atop the body having a higher durometer rating.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 2A a schematic view of an electrical return system for use with a tissue guard and electrosurgical bipolar pencil in accordance with the present disclosure;

FIG. 2B is an enlarged view of the area of detail of FIG. 2A;

FIG. 2C is an enlarged view of the area of detail of FIG. 2A; and

DETAILED DESCRIPTION

Figure 1A:
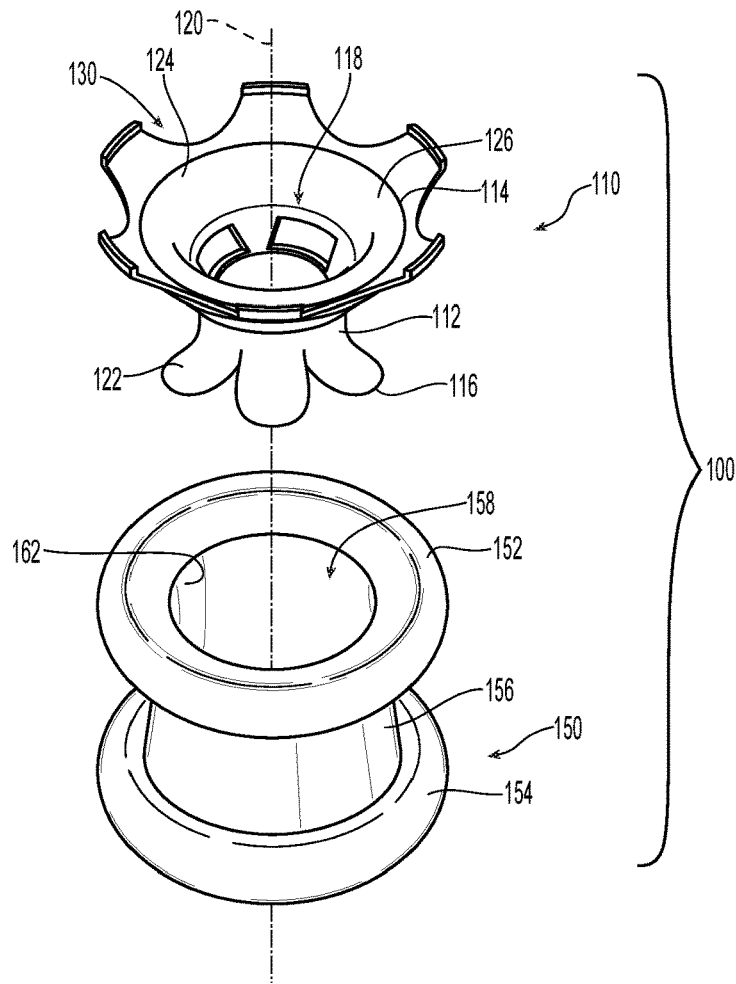
FIG. 1A is an exploded, top, perspective view of a prior art an access device and a tissue guard.
Figure 1B:
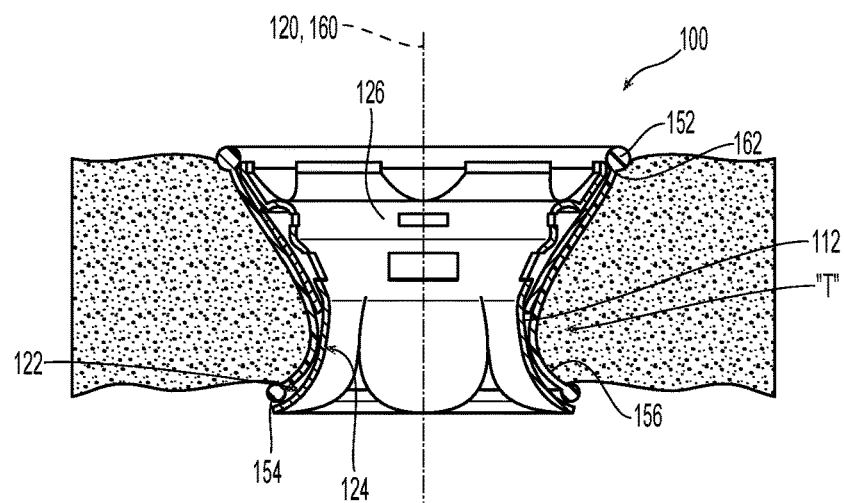
FIG. 1B is a cross-sectional view of the access device and tissue guard of FIG. 1A shown assembled and disposed within an opening in tissue.

Turning to FIGS. 1A and 1B, a prior art system 100 is shown and includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration. One or more flanges 126 are configured to secure the tissue guard to the access device 150.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Turning now to FIGS. 2A-2C, an auxiliary electrical return system for use with a tissue guard and bipolar electrosurgical pencil is shown and is generally identified as system 10. System 10 includes a cutting or tissue guard 400 and an electrosurgical pencil 200. Tissue guard 400 is similar to tissue guard 110 described above and, as such, only those elements that differ are described in detail below. Bipolar electrosurgical pencil 200 is only generally described herein and only those features necessary for a understanding of the system 10 are provided in detail. Cross reference is made to various bipolar electrosurgical pencils that may be utilized with system 10, for example, U.S. patent application Ser. No. 16/776,922 filed Jan. 30, 2020, U.S. patent application Ser. No. 16/540,593 filed Aug. 14, 2019, U.S. patent application Ser. No. 16/781,557 filed Feb. 4, 2020 and U.S. patent application Ser. No. 16/789,553 filed Feb. 13, 2020 the entire contents of each of which being incorporated by reference herein.

Tissue guard 400 includes a proximal rim 414 which is configured for engagement with an access device, for example, access device 150, an elongated body portion 412 and a distal end 416 configured for insertion within the access device 150. One or more flanges 426 are configured to engage the proximal rim 152 of the access device 150 to secure the tissue guard 400 therein. An outer surface 422 of the tissue guard 400 abuts the inner peripheral surface of the access device 150 in situ.

FIG. 2B shows an enlarged view of the distal end 416 of the tissue guard 400 wherein an electrical ground plate 425 is disposed on an inner peripheral surface 424 thereof in communication with inner lumen 418. The outer surface 422 of tissue guard 400 includes a pocket 422a defined therein configured to receive a ground wire 320 for ultimate connection at one end to the ground plate 425 and the other end to a banana plug 325 (or the like) that operably connects to an auxiliary coupling 250. Ground wire 320 provides electrical continuity between the coupling 250 and the ground plate 425. Ground plate 425 acts as an auxiliary ground return for the electrosurgical pencil 200 during use as explained in more detail below.

Electrosurgical pencil 200, in general, includes an end effector 225 attached at a distal end thereof that includes a bipolar electrical arrangement for treating tissue within the access device 150 (and tissue guard 400). Pencil 200 includes an electrical cable 305 attached at proximal end thereof which is configured to provide an active lead 305a to one electrode on the end effector 225 and a ground lead 305b on the other electrode on the end effector 225. The cable 305 is also configured to carry a switch lead 305c that connects to the pencil switch 210 for activation.

Coupling 250 includes a housing 260 having an inner bore 265 defined therein configured to receive cable 305 therethrough which ultimately connects to a plug 300 for connection to an electrosurgical generator (not shown). A flange 252 is configured to extend from the coupling 250 proximate the ground lead 305b within cable 305 and defines a plug receptacle 255 therein configured to operably receive banana plug 325 (or the like) for connection to ground wire 320 and, ultimately, to ground plate 425 as described above. Ground lead 305b electrically connects to ground wire 330 via the banana plug 325 to provide the same polarity to ground plate 425 as the return electrode in the end effector 225. As a result, the ground plate 425 acts as a secondary or auxiliary electrical return during use of the bipolar pencil 200.

In embodiments, any electrosurgical pencil 200 may be retrofitted with the coupling 250 to provide the auxiliary return. For example, the coupling 250 may include an IDC fitting (or the like) that is configured to operably engage the ground lead 305b in cable 305 in a snap fit manner. The IDC fitting includes the plug receptacle 255 that operable couples to the banana plug 325 from the ground wire 320. In this fashion, the electrosurgical pencil 200 is now configured with an auxiliary or secondary return.

FIGS. 3A-3D show an alternate tissue guard 500 for use with system 10. Tissue guard 500 includes a body 512 having a proximal end 514 and a distal end 516 configured for use with an access device 150 (as described above). Distal end 516 is generally oblong and includes a long petal 516a on one side thereof and a short petal 516b on an opposite side thereof to facilitate insertion of the tissue guard 500 into the access device 150 and an internal body cavity.

Figure 3A:
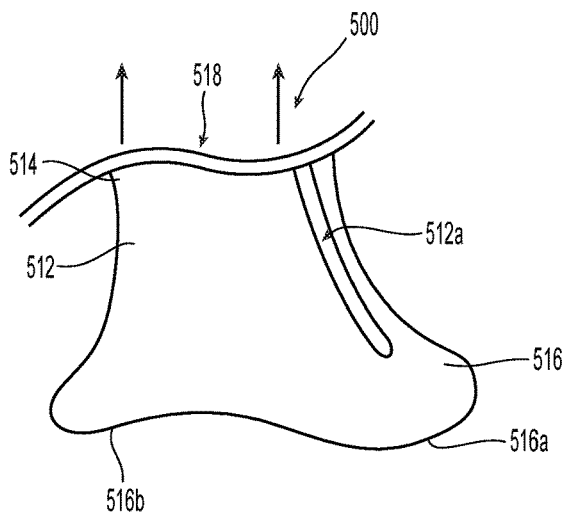
FIGS. 3A-3D show various views of another embodiment of an electrical return system for use with a tissue guard.
Figure 3B:
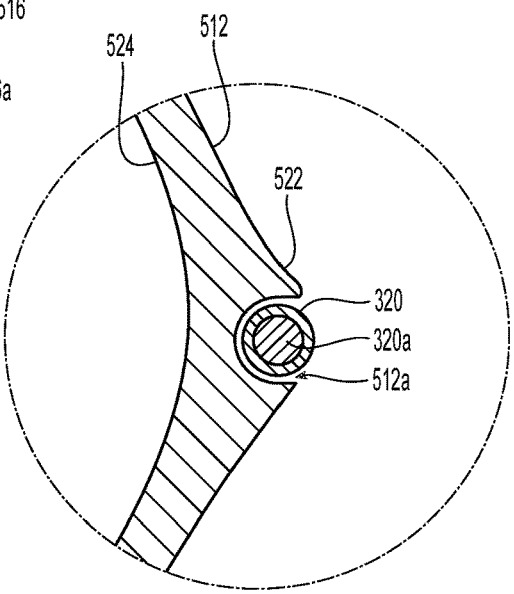
Figure 3C:
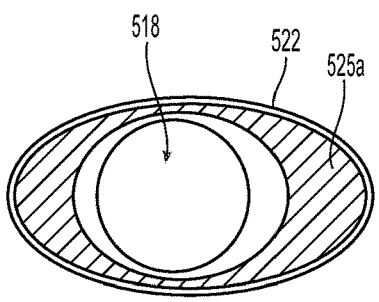
Figure 3D:
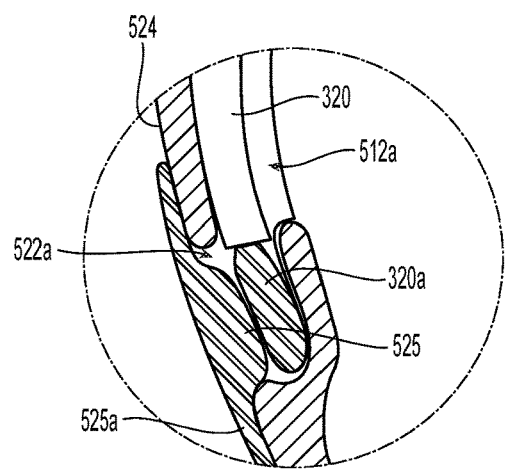

The outer peripheral surface 522 of the body 512 of the tissue guard 500 includes an elongated channel 512a defined therein and extending therealong from a point proximate the proximal end 512 to a point proximate the distal end 516 thereof (FIGS. 3A, 3C and 3D). Channel 512a is configured to receive and secure ground wire 320 therein. Channel 512a includes a pocket 522a at a distal end thereof that houses a wire connector 320a therein. Wire connector 320a is configured to operably and electrically connect to a distal end of the ground wire 320 (FIG. 3D).

Elongated channel 512a provide protection for the ground wire 320 and adds rigidity to the longer petal 516a which, in turn, facilitates insertion within the access device 150 and the surgical cavity. The elongated channel 512a may be created by adding material to the outer peripheral surface 522 to enhance robustness of the tissue guard 500. The added material may be made from a material having a higher durometer rating than the material used for the body 512 of the tissue guard 500.

Wire connector 320a is also disposed in electrical communication with a ground tab 525 disposed along an inner peripheral surface 524 of the lumen 518 of the body 512 and in general concentric registration with pocket 522a. Ground tab 525, in turn, is disposed in electrical communication with an inner conductive layer 525a deposited on a substantial portion of the inner peripheral surface of lumen 518 (FIG. 3C).

Inner conductive layer 525a may include a deposited return circuit layer (circuit formed by metal deposition technology or similar) or simply a layer of conductive material. The inner conductive layer 525a interfaces with the ground tab 525, which in turn, interfaces with the conductor 320a, which in turn, connects to the ground wire 320 which ultimately connects to the ground lead 305b from the electrosurgical device, e.g., pencil 200. As a result, the inner conductive layer 525a acts as a secondary or auxiliary electrical return during use of the electrosurgical device, e.g., pencil 200.

In embodiments, the electrically conductive layer 525a may be directly connected to the wire connector 320a eliminating the need for the ground tab 525. In this instance, during deposition, the inner conductive layer 525a is deposited on the inner periphery of the lumen 518 filling any void between the wire connector 320a within the pocket 522a.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard for use with a bipolar an electrosurgical device, comprising:
   a body defining an open proximal end, an open distal end, and a lumen extending therethrough between the open proximal end and the open distal end, the body including an elongated channel defined therealong, the elongated channel terminating in a pocket defined through an outer peripheral surface thereof, the pocket housing a wire connector therein, the distal end of the body being oblong and including a long petal and a short petal, the elongated channel providing rigidity to the long petal;
   a ground tab disposed along an inner peripheral surface of the lumen in concentric registration with the pocket and in electrical communication with the connector;
   an electrically conductive layer disposed along an inner peripheral surface of the lumen of the body, the electrically conductive layer disposed in electrical communication with the ground tab; and
   a ground wire electrically coupled at a first end to the wire connector and extending through the elongated channel to a second end adapted to electrically engage a coupling attached to a return from the electrosurgical device thereby providing electrical continuity between the electrically conductive layer and the return.

2. The tissue guard according to claim 1, wherein the electrosurgical device is an electrosurgical pencil.

3. The tissue guard according to claim 1, wherein the elongated channel is formed by adding a material atop the body to define the elongated channel on an outer peripheral surface of the body, the material having a higher durometer rating than the material used for the body.

* * * * *